(12) United States Patent
Kariv et al.

(10) Patent No.: US 9,675,302 B2
(45) Date of Patent: Jun. 13, 2017

(54) PROLAPSE DETECTION AND TOOL DISLODGEMENT DETECTION

(75) Inventors: Itay Kariv, Haifa (IL); Amit Cohen, Binyamina (IL)

(73) Assignee: MediGuide Ltd., Haifa (IL)

( * ) Notice: Subject to any disclaimer, the term of this patent is extended or adjusted under 35 U.S.C. 154(b) by 1506 days.

(21) Appl. No.: 12/651,148

(22) Filed: Dec. 31, 2009

(65) Prior Publication Data

US 2011/0160570 A1    Jun. 30, 2011

(51) Int. Cl.

| | |
|---|---|
| *A61B 5/05* | (2006.01) |
| *A61B 6/12* | (2006.01) |
| *A61B 5/00* | (2006.01) |
| A61B 5/06 | (2006.01) |
| A61B 5/11 | (2006.01) |
| A61B 6/00 | (2006.01) |
| A61B 8/08 | (2006.01) |
| A61B 34/20 | (2016.01) |

(52) U.S. Cl.
CPC ............. *A61B 6/12* (2013.01); *A61B 5/721* (2013.01); *A61B 8/5276* (2013.01); A61B 5/06 (2013.01); A61B 5/1114 (2013.01); A61B 5/7289 (2013.01); A61B 6/527 (2013.01); A61B 8/0833 (2013.01); A61B 34/20 (2016.02)

(58) Field of Classification Search
None
See application file for complete search history.

(56) References Cited

U.S. PATENT DOCUMENTS

| | | | |
|---|---|---|---|
| 5,443,457 A | 8/1995 | Ginn et al. | |
| 6,233,476 B1 | 5/2001 | Strommer et al. | |
| 6,263,230 B1 | 7/2001 | Haynor et al. | |
| 6,332,089 B1 * | 12/2001 | Acker et al. | 600/424 |

(Continued)

FOREIGN PATENT DOCUMENTS

| | | | |
|---|---|---|---|
| WO | WO 2007/002084 | * | 1/2007 |
| WO | WO 2007/036925 | * | 4/2007 |

OTHER PUBLICATIONS

"Internatonal Search Report and Written Opinion of the International Searching Authority", PCT/US2010/050231 Nov. 18, 2010.

*Primary Examiner* — Christopher Cook
(74) *Attorney, Agent, or Firm* — Dykema Gossett PLLC

(57) ABSTRACT

A tool dislodgement detection apparatus includes an MPS outputting position and orientation (P&O) readings for determining tool motion. A control generates an alarm based on the tool motion and dislodgement criteria. The criteria includes whether the tool motion meets a condition based on the type of medical procedure or tool, the tool parking position, a patient characteristic (e.g., age, weight, gender) or a physician preference. The criteria includes when the correlation between the tool motion and the cardiac, respiration and patient motion changes abruptly. In a prolapse detection apparatus, guidewire tip P&O readings determine a tip motion vector. The control generates an alarm using the motion vector and predetermined criteria. The criteria include a substantial change in the tip orientation not accompanied by a corresponding position change and a change in the motion vector by about 180° accompanied by a corresponding position change no greater than a threshold.

25 Claims, 9 Drawing Sheets

(56) References Cited

U.S. PATENT DOCUMENTS

| | | | |
|---|---|---|---|
| 6,473,635 B1* | 10/2002 | Rasche | A61B 5/06 600/424 |
| 6,498,944 B1 | 12/2002 | Ben-Haim et al. | |
| 6,507,751 B2* | 1/2003 | Blume et al. | 600/424 |
| 6,773,446 B1 | 8/2004 | Dwyer et al. | |
| 6,788,967 B2 | 9/2004 | Ben-Haim et al. | |
| 6,807,439 B2 | 10/2004 | Edwards et al. | |
| 7,197,354 B2 | 3/2007 | Sobe | |
| 7,343,195 B2 | 3/2008 | Strommer et al. | |
| 7,386,339 B2 | 6/2008 | Strommer et al. | |
| 2003/0187369 A1 | 10/2003 | Lewis et al. | |
| 2004/0097806 A1* | 5/2004 | Hunter et al. | 600/434 |
| 2006/0058647 A1* | 3/2006 | Strommer et al. | 600/434 |
| 2008/0161681 A1 | 7/2008 | Hauck | |
| 2008/0275467 A1* | 11/2008 | Liao | A61B 6/032 606/130 |
| 2009/0030307 A1* | 1/2009 | Govari et al. | 600/424 |
| 2009/0306536 A1* | 12/2009 | Ranganathan et al. | 600/549 |
| 2010/0121167 A1* | 5/2010 | McGarraugh | 600/347 |

* cited by examiner

| TOOL MPS (#1) | TOOL MPS (#2) | PATIENT PRS | PATIENT ECG |
|---|---|---|---|
| P & O #1 | P & O #1 | P & O #1 | SIG. #1 |
| P & O #2 | P & O #2 | P & O #2 | SIG. #2 |
| ⋮ | ⋮ | ⋮ | ⋮ |
| P & O #n | P & O #n | P & O #n | SIG. #3 |

FIG.5

PROLAPSE DETECTION AND TOOL DISLODGEMENT DETECTION

BACKGROUND OF THE INVENTION a. Field of the Invention

The instant invention relates generally to detection methods for use in medical systems. In particular, the instant invention relates to prolapse and tool/device dislodgement detection systems and methods.

b. Background Art

It is known to park a medical tool/device within the body of a patient, for example, during a medical procedure. The tool/device is usually considered parked when the tool is inserted into a structure like an artery or a vein and has reached a desired location. For example, a cannulation catheter used for left-heart lead implantation may be parked inside the coronary sinus. Alternatively, the tool/device may be deemed parked when the tool is affixed to the tissue at a desired location. There are other examples where a medical tool or device is parked inside the body of a patient, for example, where a reference electrode is parked at a desired location to provide a stable reference point or origin for a navigation and localization system (e.g., parking a navigational reference catheter so that by moving a mapping catheter within a heart chamber coordinates may be acquired). Unfortunately, it is also known that a parked or stationary medical tool/device may become dislodged during the procedure, for example, by an external force being applied against the parked medical tool. U.S. Patent Publication 2008/0161681 entitled NAVIGATIONAL REFERENCE DISLODGEMENT DETECTION METHOD & SYSTEM to Hauck, assigned to the common assignee of the present invention and hereby incorporated by reference in its entirety, disclose a system for monitoring for dislodgement of a navigational reference electrode away from an initial (desired) reference location.

It is also well known to advance a guidewire through a patient's vasculature to a destination site and then to insert and advance a catheter or other tool to the site with the aid of the guidewire. During this process, however, the guidewire tip may prolapse, or in other words, the guidewire distal tip may bend or fold on itself (i.e., back along its route). Guidewire tip prolapse may occur when the guidewire is accidentally inserted into a branch in the blood vessel (i.e., the guide tip being caught in a bifurcation) or when the guidewire tip encounters a blockage in the blood vessel turning the tip back against itself (i.e., back along its route) inside the blood vessel. Traditionally, the process of advancing the guidewire is performed under constant fluoroscopy, which allows a physician to immediately identify any prolapse of the guidewire tip. It is therefore known to detect guidewire prolapse through visual recognition by the physician using live fluoroscopy. While detection using this approach is accurate, it would nonetheless be desirable to reduce or eliminate the need for (or amount of) live fluoroscopy so as to reduce patient exposure while at the same time retaining the capability of recognizing guidewire prolapse.

There is therefore a need to minimize or eliminate one or more of the problems set forth above.

BRIEF SUMMARY OF THE INVENTION

One advantage of the methods and apparatus described, depicted and claimed herein involves the capability for detection of medical tool/device dislodgement from a reference location as well as for detection of a guidewire prolapse condition, both with little or no exposure to X-rays such as used in live fluoroscopy. Another advantage of the methods and apparatus described, depicted and claimed herein involves the capability of faster identification of dislodgement as well as offloading from the physician the burden of monitoring for dislodgements. A still further advantage of the methods and apparatus described, depicted and claimed herein involves the capability of identifying an impending dislodgement, which provides for an alert before the dislodgement.

The present disclosure, in a first aspect, is directed to an apparatus for detecting dislodgement of a medical tool/device from a reference location within a patient's body. The dislodgement detection apparatus includes a localization system configured to output a location reading (e.g., comprising at least one of a position and orientation (P&O)) of the tool in a coordinate system. The localization system outputs a plurality of location readings over time, which is used by a control (e.g., processor) to determine a motion of the tool. The control generates an alarm signal indicative of dislodgement when the tool motion meets predetermined dislodgement detection criteria. In an embodiment, the predetermined detection criteria includes one or more conditions on the motion of the tool determined according to at least one factor selected from the group comprising the type of medical procedure, the type of medical tool, the parking position of the medical tool, a characteristic of the patient (e.g., age, weight or gender) and a preference of a physician using the apparatus. Generally, when the criticality of the motion to the outcome of the medical procedure is higher, a threshold defining the level of permitted tool motion before alarm will correspondingly be lower.

In another embodiment, detection is accomplished through assessing the correlation of the tool motion relative to signals indicative of the motion of the reference location. The parked tool and the reference location may both be moving during a medical procedure due to such influences as patient respiration-induced movement, gross patient (body) movement as well as heartbeat induced movement. Therefore, tool movement alone does not always indicate dislodgement. Therefore, the detection apparatus distinguishes between situations where the respective movements of the tool and reference location indicate dislodgement versus situations where the respective movements indicate movement together (i.e., no relative movement and thus no dislodgement).

The control is configured with a detection block to determine, during a learning stage when the tool is parked at the reference location, a first correlation between the tool motion, on the one hand, and the motion of the reference location within the body, on the other hand. Signals indicative of the motion of the reference location may also be used. At times after the learning stage, the control monitors a second correlation between the tool motion and reference location motion. The control generates an alarm signal indicative of dislodgement when a comparison of the first correlation and the second correlation meets predetermined dislodgement detection criteria (e.g., when the correlation changes "abruptly").

In an embodiment, patient respiration and gross patient (body) movements, which can influence the movement of the parked location, can be determined from a series of location readings from a patient reference sensor (PRS). Additionally, patient heartbeat movements, which can also influence movement of the parked location, can be indicated by an electrocardiogram (ECG) signal(s). The detection block learns the tool motion and determines when the correlation between the tool motion (i.e., as indicated by the tool location readings) and the motion of the reference location (i.e., as indicated by the PRS location readings and the ECG signal) changes significantly enough to indicate dislodgement. When the tool and the reference location are both relatively still or are both moving together, the correlation should be high. However, when there is relative movement (i.e., dislodgement), the correlation should decrease abruptly and the control detects this change and generates the alarm signal.

The present disclosure, in a second aspect, is directed to an apparatus for detecting a prolapse condition of a guidewire. The apparatus includes a localization system configured to output position and orientation (P&O) readings indicative of the P&O of a distal tip of the guidewire, which are used by a control (e.g., a processor) to determine a tip motion vector. The control is configured to generate an alarm signal indicative of a prolapse condition using the determined tip motion vector and predetermined prolapse detection criteria. In an embodiment, the control is configured with a detection block arranged to assess prolapse detection criteria that may include determining when change in the tip orientation exceeds a predetermined minimum that is not accompanied by a corresponding change in the tip position. For example, this situation may occur when the guidewire tip is caught on a bifurcation. The criteria may also include determining when a change in the tip motion vector in the one-hundred and eighty degree range is accompanied by at most only a small corresponding change in the tip position (e.g., no greater than a predetermined threshold such as a blood vessel diameter). For example, this situation may be occur when the guidewire encounters an obstruction in a vessel and turns back on itself.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 5 is a chart showing P&O readings representing the tool motion as well as PRS P&O readings and ECG signal samples associated with the patient motion.

DETAILED DESCRIPTION OF THE INVENTION

Figure 1:
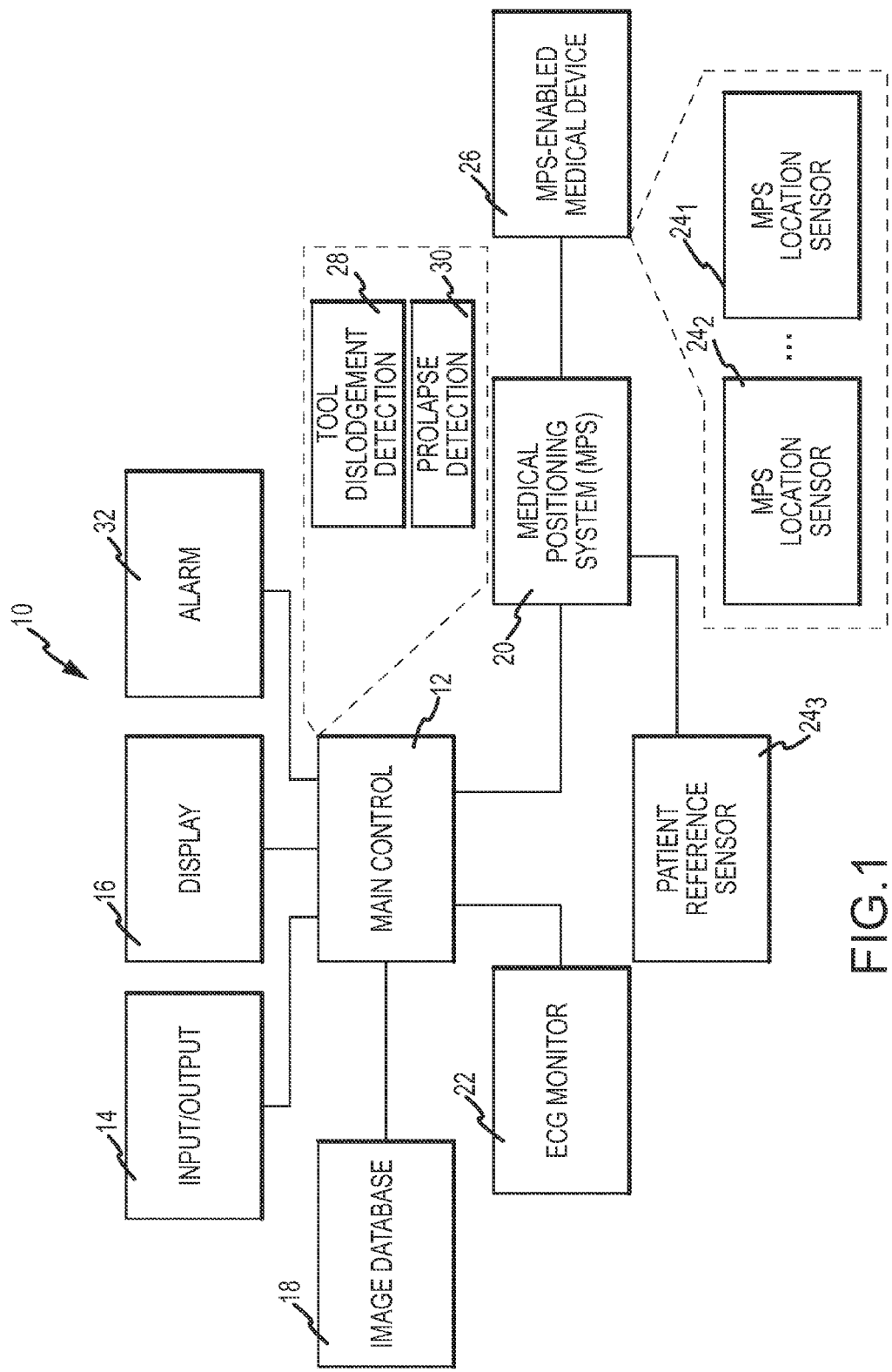
FIG. 1 is a schematic and block diagram view of a system incorporating guidewire prolapse and medical tool dislodgement detection embodiments.

Referring now to the drawings wherein like reference numerals are used to identify identical components in the various views, FIG. 1 is a diagrammatic view of a system or apparatus 10 in which aspects of tool dislodgement detection and guidewire prolapse detection may be embodied. It should be understood that while embodiments will be described in connection with a magnetic field-based positioning system deployed in connection with a fluoroscopy-based imaging environment, this is exemplary only and not limiting in nature.

As described in the Background, there is a desire to reduce a patient's exposure to x-rays, such as may be used in live fluoroscopy. It is therefore desirable to be able to detect medical tool dislodgement detection and/or guidewire prolapse without the use of (or with reduced use of) fluoroscopy. The methods and apparatus described herein will therefore reduce the need for continuous exposure or subsequent additional exposures for detection purposes.

With continued reference to FIG. 1, the system 10 as depicted includes a main control 12 (e.g., a processor) having various input/output mechanisms 14, a main display 16, an optional image database 18, a localization system such as a medical positioning system (MPS) 20, an electrocardiogram (ECG) monitor 22, a plurality of MPS location sensors respectively designated $24_1$, $24_2$ and $24_3$, and an MPS-enabled medical tool/device 26 (which itself includes one or more MPS location sensors $24_1$, $24_2$). Hereinafter, reference to the term medical tool may be taken to mean a medical tool, a medical device or a combination thereof.

The control 12, in a computer-implemented embodiment, is programmed to perform a plurality of functions, including a medical tool dislodgement detection function 28 (hereafter sometime detection block 28) and a guidewire prolapse detection function 30 (hereinafter sometimes detection block 30). The control 12 is configured generally to generate an alarm signal 32 (shown as alarm block 32 in FIG. 1) in response to the predetermined criteria being satisfied indicating detection of either (1) medical tool dislodgement or (2) guidewire prolapse. The input/output mechanisms 14 may comprise conventional apparatus for interfacing with a computer-based control, for example, a keyboard, a mouse, a tablet or the like. The display 16 may also comprise conventional apparatus.

Embodiments consistent with the invention may find use in applications that display imaging of a region of interest and therefore the system 10 may include the image database 18. The image database 18 may be configured to store image information relating to the patient's body, for example a region of interest surrounding a reference location where a medical tool has been parked or alternatively a region of interest surrounding a location where a guidewire prolapse condition has been detected. The image data in the database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from the ECG monitor 22. It should be understood that the foregoing are examples only and not limiting in nature. It should be further understood that the images may be acquired through any imaging modality, now known or hereafter developed, for example X-ray, ultrasound, computerized tomography, nuclear magnetic resonance or the like.

The MPS 20 is configured to serve as the localization system and to determine positioning (localization) data associated with one or more MPS location sensors and outputting a respective location reading, which may include at least one or both of a position and an orientation (P&O) relative to a reference coordinate system. In turn, the P&O may be expressed as a position (i.e., a coordinate in three axes X, Y and Z) and orientation (i.e., an azimuth and elevation) of the magnetic field sensor in the magnetic field relative to a magnetic field generator(s)/transmitter(s). Other expressions of a P&O (e.g., other coordinates systems) are known in the art and fall within the spirit and scope of the present invention (e.g., see for example FIG. 3 and associated text of U.S. Pat. No. 7,343,195 entitled "METHOD AND APPARATUS FOR REAL TIME QUANTITATIVE THREE-DIMENSIONAL IMAGE RECONSTRUCTION OF A MOVING ORGAN AND INTRA-BODY NAVIGATION" to Strommer et al, incorporated by reference in its entirety; location [X, Y, Z] and orientation (angles α, β, and χ)).

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. The ECG signal(s) from the monitor 22 may be used as an input to the medical tool dislodgement detection block 28 for detecting when a medical device 26 has become dislodged from a reference location, as described in greater detail below. More generally, the ECG signal(s) may also be used by the control 12 for ECG synchronized play-back of a previously captured sequences of images (cine loop). The ECG monitor 22 and ECG-electrodes may comprise conventional components.

The MPS location sensor $24_1$, and optionally MPS location sensor $24_2$, are associated with the MPS-enabled medical device 26. In a tool dislodgement detection embodiment, the device 26 may comprise a wide variety of medical tools 26a (best shown diagrammatically in FIG. 3), including conventional tools such as a catheter (e.g., a cannulation catheter for a left-heart lead implantation procedure, a guiding catheter, a CS catheter, or an EP catheter for a variety of diagnostic and/or therapeutic procedures), an introducer, EP study devices (e.g., HIS, AV, etc.) and other known tools.

In a prolapse detection embodiment (best shown diagrammatically in FIGS. 6A-6E and 7), the device 26 may comprise a guidewire 26b or the like. In both embodiments, the MPS location sensor $24_1$ and optional MPS location sensor $24_2$ each detect one or more characteristics of the magnetic field in which they are disposed wherein the MPS 20 is configured to provide (output) a respective position and orientation (P&O) indicative of the MPS sensor's three-dimensional position and orientation in a so-called motion box.

The patient reference sensor (PRS) $24_3$ is configured to provide a positional reference of the patient's body so as to determine gross patient body movements and/or respiration-induced movements. This information may be used by the main control 12 for a variety of purposes, including in the detection approaches described herein and for motion compensation, to name a few. The PRS $24_3$ may be attached to the patient's manubrium sternum, a stable place on the chest, or other location that is relatively positionally stable. Like the MPS location sensors, the PRS $24_3$ is also configured detect one or more characteristics of the magnetic field in which it is disposed wherein the MPS 20 is configured to provide a position and orientation (P&O) indicative of the PRS's three-dimensional position and orientation in the motion box in the reference coordinate system.

In a magnetic field-based embodiment, the P&O may be based on capturing and processing the signals received from the magnetic field sensor while in the presence of a controlled low-strength AC magnetic field. The internal sensors may each comprise one or more magnetic field detection coil(s), and it should be understood that variations as to the number of coils, their geometries, spatial relationships, the existence or absence of cores and the like are possible. From an electromagnetic perspective—all sensors are created equal: voltage is induced on a coil residing in a changing magnetic field, as contemplated here. The sensors 24 are thus configured to detect one or more characteristics of the magnetic field(s) in which they are disposed and generate an indicative signal, which is further processed by the MPS 20 to obtain the P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety.

Figure 2:
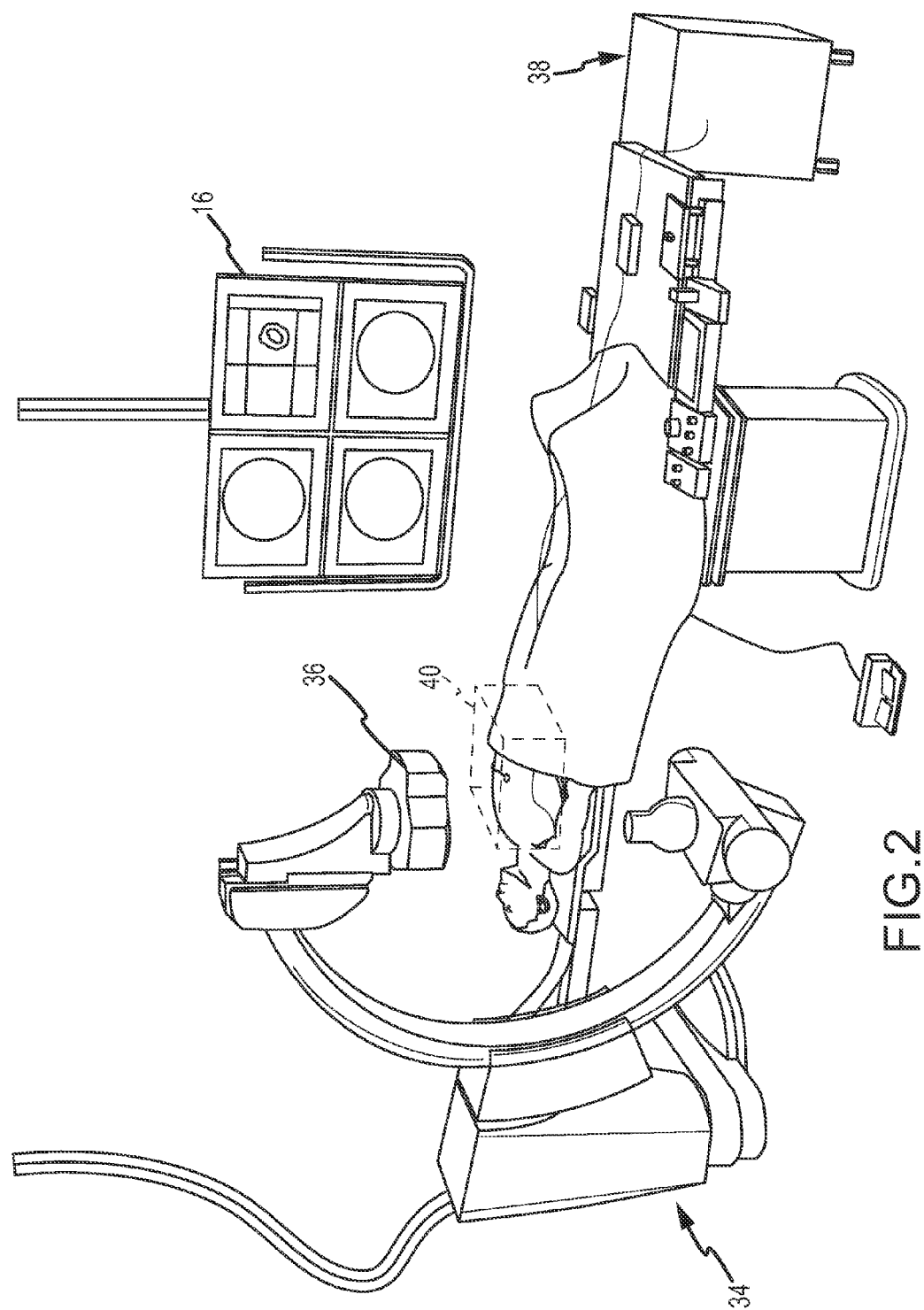
FIG. 2 is a diagrammatic view of the system of FIG. 1 in a fluoroscopy-based imaging environment.

FIG. 2 is a diagrammatic view of the system 10 as incorporated into a larger system that has self-contained imaging capability. It should be understood that while the detection approaches described herein do not require the use of fluoroscopy, other aspects of any medical procedure may involve such use, at least intermittently. The system 10 is shown as being incorporated into an fluoroscopic imaging system 34, which may include commercially available fluoroscopic imaging components (i.e., "Catheter Lab"). The MPS system 20, in a magnetic field-based embodiment, includes a magnetic transmitter assembly (MTA) 36 and a magnetic processing core 38 for determining position and orientation (P&O) readings. While the MTA 36 is fixed to the C-arm in the illustrative embodiment, it should be understood that other variations are possible, including embodiments where the MTA 36 is mounted elsewhere (e.g., under the table). The MTA 36 is configured to generate the magnetic field(s) in and around the patient's chest cavity, in a predefined three-dimensional space designated a motion box 40 in FIG. 2. The MPS sensors $24_i$ (where i=1, 2, . . . , n) as described above are configured to sense one or more characteristics of the magnetic field(s) and each generate a respective signal that is provided to the magnetic processing core 38. In one embodiment, the MPS 20 is configured so that when the sensors are in the motion box 40, the amplitude of the sensed signal is large enough to ensure accurate position determination. The processing core 38 is responsive to these detected signals and is configured to calculate respective three-dimensional position and orientation (P&O) readings for each MPS sensor $24_i$ in the motion box 40. Thus, the MPS system 20 enables real-time tracking of each sensor $24_i$ in three-dimensional space. The positional relationship between the image coordinate system and the MPS coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is imported from an external source, a registration step may need to be performed initially. One exemplary embodiment of an MPS system 20 will be described in greater detail below in connection with FIG. 8.

The control 12 is configured by way of the dislodgement detection block 28 to function as a medical tool dislodgement detection apparatus. The detection block 28 provides the capability of detecting when a medical tool 26a that is parked at a reference location in a patient's body has moved away from that reference location by at least a predetermined threshold amount. The MPS 20 is configured to monitor the position of the one or more MPS location sensors attached to or incorporated within the medical tool 26a. The control 12 generates an alarm signal (e.g., which may be an alert to a physician) when the medical tool 26a is about to or has become dislodged, based on the processing of the MPS data and, optionally, other relevant data (e.g., PRS P&O readings and the ECG signal).

Figure 3:
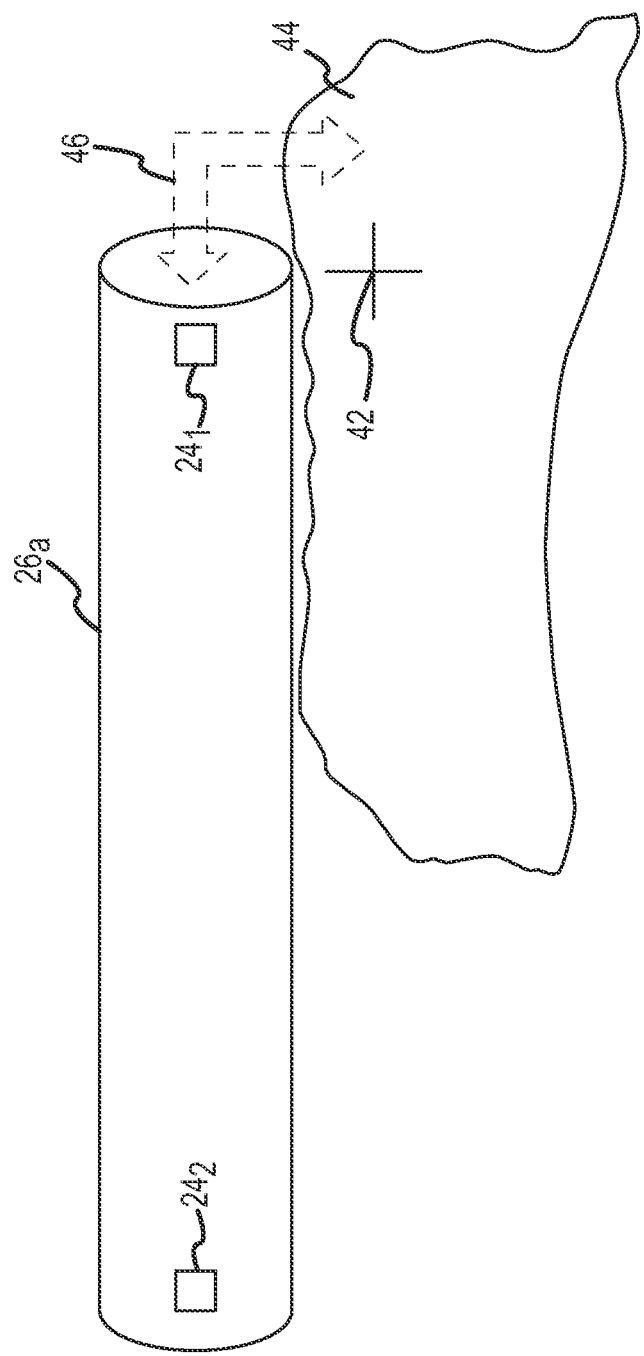
FIG. 3 is a diagrammatic view of a medical tool parked relative to a reference location within the body of a patient.

FIG. 3 is a diagrammatic view of a medical tool 26a. The medical tool 26a includes a first MPS location sensor $24_1$ that is coupled to a distal end of the tool 26a and optionally a second MPS location sensor $24_2$ is coupled at another location more proximal of sensor $24_1$ and may be at the proximal end of the tool 26a. Each of the MPS location sensors $24_1$ and $24_2$ are coupled (e.g., by wire conductor) to the MPS 20, which is remotely situated (see FIG. 1). Tool 26a may be equipped with still further MPS location sensors (not shown).

Also shown is a reference location 42 located within the patient's body (i.e., tissue 44 being illustrated for context). The reference location 42 corresponds to a location in the patient's anatomy and may have (or be determined to have) a predetermined three-dimensional position in a reference coordinate system, i.e., an [X, Y, Z] coordinate in a Cartesian reference coordinate system having an arbitrary origin. The arbitrary origin may be, for example only, the location of the MTA 36 in the MPS system 20, a location on the motion box 40 or any other known location. Although not shown, the reference location 42 may also have an orientation associated therewith, applicable to the orientation that the parked tool adopts when properly parked. During a medical procedure, a physician (not shown) positions the medical tool 26a within the patient's body. The physician then parks the medical tool 26a at the predetermined reference location 42. The term parked may mean a situation when the tool is in the desired location (i.e., like an artery or vein), although it should be understood that a more positive means of attachment may also be involved, shown schematically as attachment 46 in FIG. 3.

With continued reference to FIG. 3, in one embodiment, the detection block 28 of control 12 is configured to determine whether the tool 26a has become dislodged from its reference (parked) position by detecting when predetermined motion conditions imposed on the motion of the medical tool 26a have been satisfied. This embodiment may have particular application where the reference location exhibits little movement or less than would be anticipated to be problematic given a medical procedure), or alternatively where the position of the reference location can be adjusted (i.e., compensated for) so as to remove the effects of such movement relative to the movement of the medical tool, making the assessment of the tool motion alone a valid indicator of tool dislodgement.

In this embodiment, when the motion (i.e., a change in position, orientation or both) of the MPS location sensor $24_1$ exceeds a predetermined threshold value, the detection block 28 determines that the medical tool 26a has become dislodged or is about to become dislodged and as described above, generates the alarm signal (alarm block 32). The predetermined conditions are determined according to one or more factors selected from the group comprising the type of medical procedure, the type of medical tool, the parking position of the medical tool, a characteristic of the patient and a preference of a physician using the apparatus. In turn, the characteristic of the patient may be one selected from the group comprising age, weight and gender.

As an example, in a type of medical procedure where the motion of the inspected anatomy is higher, the alarm threshold will be set higher. Also, where the criticality of the motion to the outcome of the procedure is higher, the alarm threshold will be set lower, perhaps knowingly increasing the probability of false alarms. For example, where the parked tool serves as a reference for the treatment of chronic total occlusion (CTO) in coronary arteries, where accuracy is critical, less motion will be allowed and the threshold will be set lower. In contrast, in procedures like CRM lead placement where a greater amount of motion can be tolerated, the threshold can be set higher before an alarm is generated. As to the type of medical tool, in general, a larger medical tool 26a will be allowed a greater magnitude of motion (movement from the reference location) without producing an alarm. As to physician preferences, the physician may set the threshold to allow only a relatively small amount of motion (i.e., a small amount of "dislodgement" relative to the "parked" position), in which case the system will provide better indications but with perhaps more false alarms being anticipated. On the other hand, if the physician sets the threshold to allow an increased amount of dislodgement or displacement from the "parked" position, fewer false alarms would be anticipated but a true occurrence of dislodgement may go undetected. In this variation, the physician (user) expresses his/her own preferences in the setting of the threshold levels. Additionally, the actual values of the threshold levels may also be influenced by clinical factors (e.g., how deep in the vessel the device is parked, the width of the vessel in the parking location, the stiffness of the device, etc.).

The particular values, which if exceeded would trigger an alarm, will vary, for example, based on the factors set forth above. In many instances, where the ultimate parameter to be monitored is a physical distance (e.g., a tool dislodgement moving away from the reference location by a predetermined distance such as 1 mm), such values for the tool motion conditions may be determined empirically (e.g., bench testing). Additionally, determining the level of change in orientation (i.e., a predetermined level) may be indicative of an impending dislodgement may also be determined empirically.

In sum, the MPS 20 is configured to produce location readings of the device 26, which readings are constantly motion compensated for various movements, such as patient body movements, respiration movements, cardiac movements and the like. The control unit 12 (through dislodgement detection block 28) is configured to monitor subsequent motion-compensated location (i.e., position and orientation) readings indicating the subsequent locations of the device 26 and determine any changes in the subsequent device P&O versus the corresponding device P&O when the device was "parked" (i.e., the parking location or parking P&O of the device). This is a comparison step. Finally, the control unit 12 (through dislodgement detection block 28) determines whether the changes (if any) meet any of the dislodgement detection criteria (e.g., such as a motion condition or a predetermined change in orientation, etc.). If so, the control unit 12 generates an alarm.

Figure 4:
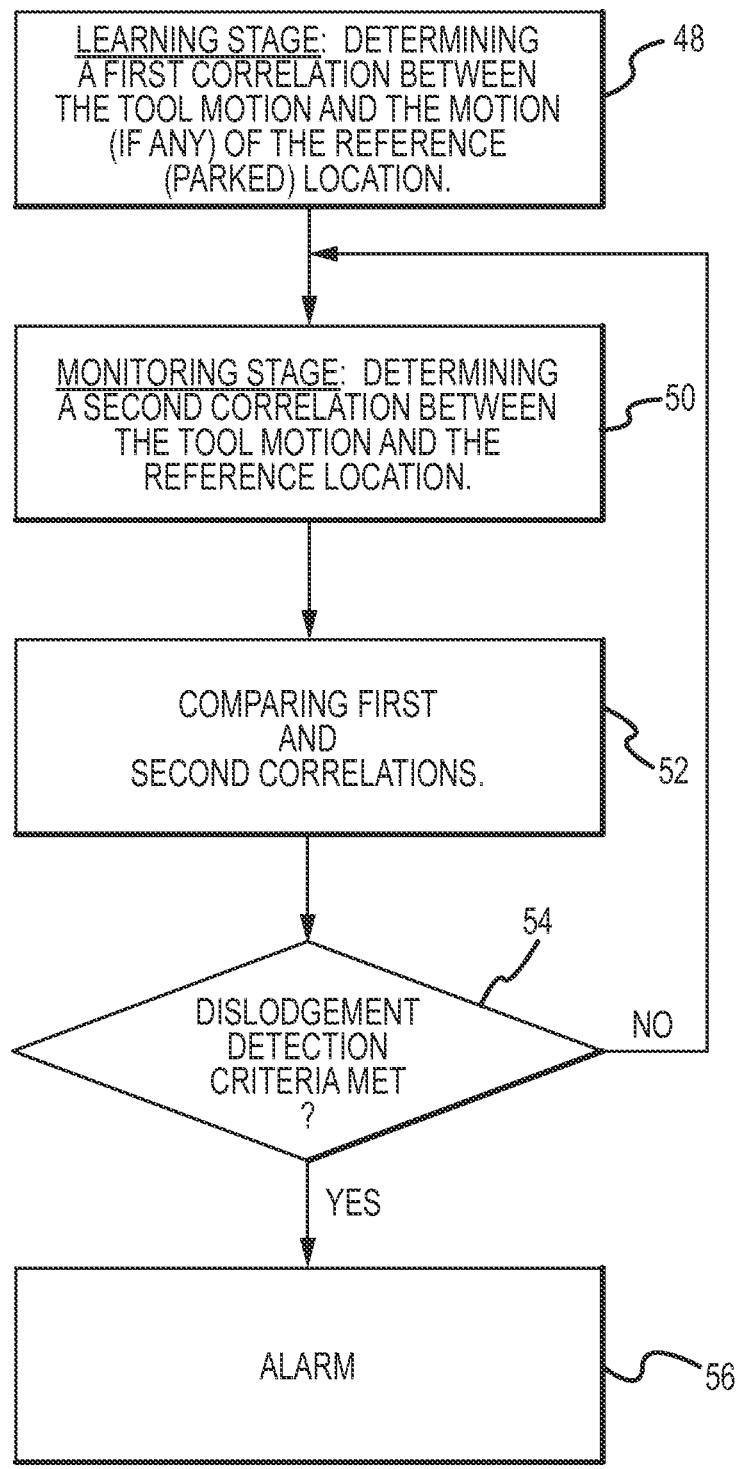
FIG. 4 is a flowchart showing a method for tool dislodgement detection.

FIG. 4 is a flowchart showing a method, in another embodiment, for detecting dislodgement of a medical tool. While the embodiment described above focuses on whether conditions on the tool motion have been satisfied, the embodiment to be described below further accounts for the motion of the patient's body in the region of interest surrounding the reference (parked) location. The method begins in step 48.

In step 48, the detection block 28 of control 12, in response to an initialization event, begins a learning stage. The initialization event may be the receipt of an input start signal through an input/output interface, for example, as initiated by the physician. Alternatively, the initialization event may occur automatically when predetermined tool motion conditions have been met (e.g., when the medical tool 26a has been in the same position for a time period exceeding a predetermined value). The learning stage in step 48 involves signaling the MPS 20 to begin monitoring the location (i.e., at least one or both of the P&O) of the MPS sensor $24_1$, thereby also monitoring the position of the distal tip of the tool 26a. Note, in this description, it is the distal tip of the tool 26a that is parked at the reference location 42, although this relationship is exemplary only (i.e., a position on the tool offset from the tip could be parked at the reference location). A series of location (P&O) readings indicative of the location of the distal tip of the tool 26a may be recorded for further assessment by the detection block 28.

The parked tool and the reference (parked) location may both be moving during a medical procedure due to such motion influences as patient respiration-induced movement, gross patient (body) movement as well as heartbeat-induced movement. Therefore, movement of the tool alone (e.g., as indicated by the tool P&O readings) does not always indicate dislodgement. Therefore, the detection block 28 is further configured to distinguish between situations where the respective movements of the tool and reference location indicate dislodgement versus those situations where the tool and reference location are moving together but no relative movement therebetween and thus no dislodgement. At a general level, the detection block 28 distinguishes between these two situations by first determining (learning) the tool motion and then determining a baseline correlation (i.e., a first correlation) between the tool motion and the motion of the reference (parked) location 42. Note that the tool is "parked" when the medical tool 26a has not moved from reference location 42, or even if the medical tool 26a is moving, it is moving together with the reference location (i.e., part of the patient's anatomy) such that the tool is still deemed, effectively, parked. When the tool is parked, therefore, the correlation between the tool motion and any heartbeat-induced, respiration-induced and gross patient body movements on the reference (parked) location should be relatively high. One approach for determining such a correlation is to compare the tool P&O's with various signals indicative of possible motion of the reference location, such as the PRS P&O readings and samples of the ECG signal. Once the detection block 28 determines the first correlation the method proceeds to step 50.

In step 50, the detection block 28 begins a monitoring stage, where a second correlation is determined between the tool motion and the motion of the reference location within the patient's body. The monitoring stage time period typically occurs during the medical procedure itself. The method proceeds to step 52.

In step 52, the detection block 28 compares the first (baseline) correlation and second correlation obtained in step 48 (learning stage) and step 50 (monitoring stage), respectively. The method proceeds to step 54.

In step 54, the detection block 28 determines, based on the comparison of the first correlation and the second correlation whether predetermined dislodgement detection criteria has been met. If the dislodgement detection criteria has not been met ("NO"), then the method branches to step 50 for continued monitoring by the tool dislodgement detection logic. However, if the detection block 28 determines that the dislodgement detection criteria has been met, then the method branches to step 56.

In step 56, the detection block 28 signals the main control 12 to generate an alarm signal (alarm block 32) when the predetermined dislodgement detection criteria has been met. The alarm block 32 may take any one or more different alerting or alarming mechanisms known in the art. For example, the alarm 32 may comprise a visual indication, an audible indication (i.e., either verbal or non-verbal), a tactile indication or a combination of one or more of the foregoing indications.

FIG. 5 is a table showing medical tool P&O data, PRS P&O data and ECG signal data. The detection block 28 is configured to determine the correlation between tool motion and reference location motion by in turn determining the correlation between signals indicative of the tool motion (e.g., tool P&O readings) and data/signals indicative of (or having influence on) the motion of the reference location within the body (e.g., PRS P&O readings and ECG signal data). FIG. 5 is a table having several columns of data. A first column of data comprising a first series of P&O readings 58 that is indicative of the motion of the medical tool 26a (e.g., distal tip when the first MPS location sensor $24_1$ is located at or near the distal tip). A second, optional column of data comprises a second series of P&O readings 60 that is also indicative of the motion of the medical tool 26a (e.g., the proximal end when the second MPS location sensor $24_2$ is located at or near the proximal end). A third column of data comprises a third series of P&O readings 62 that is indicative of respiration-induced movements of the patient as well as any gross (body) movements of the patient, which may be indicative of or have an influence on the motion of the reference location. A fourth column of data comprises a series of patient ECG signal(s) readings/samples 64 that is indicative generally of the mechanical (physical) movements of the heart and is indicative of (or may have an influence on) the motion of the reference location 42.

The dislodgement detection block 28 of the control 12 is configured to distinguish between two situations: (1) where the tool 26a moves at the same time as the reference location 42 within the body but which does not indicate dislodgement (i.e., the tool and the reference (parked) location move "together" so there is no relative movement and no dislodgement); and (2) where the tool 26a moves at the same time as the reference location 42 within the body but which does indicate dislodgement. The detection block 28 is configured to learn (i.e., above "learning" stage—step 48 of FIG. 4) the tool motion and then determine the correlation between such tool motion and the motion of the reference location 42 when the tool is parked. In an embodiment, the detection block 28 determines the correlation between the tool motion and the cardiac, respiratory and patient (body) motion, where the latter movements are approximated by the series of patient PRS readings 62 and ECG readings 64. When the tool is parked, the correlation should be very high. When the correlation changes by more than a predetermined amount during a predetermined time period, such an "abrupt" change is deemed indicative of tool dislodgement.

One approach for determining correlation may be to compare the respective motions relative to a common timeline. For example, over some time interval, the detection block 28 may track the motion of the device 26a, as indicated by the detected P&O's readings (series 58 in FIG. 5) in addition to tracking the respiratory and gross patient (body) motion and cardiac motion via data series 62 (PRS) and series 64 (ECG), respectively.

Thus, the detection block 28 is configured to determine a first correlation between the tool motion and the motion of the reference location 42 during a first, learning stage when the tool is parked, e.g., in the case of a location in or near the heart, by reference to the indicative signals such as the PRS sensor output and the ECG signal(s) readings. Then, during a monitoring stage after the learning stage, the detection block 28 constantly monitors the relevant signals and determine a second correlation. When the second correlation changes abruptly relative to the first correlation, then the detection block 28 detects dislodgement.

The particular amount of correlation change, and the period in which such a change must occur, which if exceeded would trigger an alarm, will vary based on the same factors as set forth above (e.g., procedure type, tool type, etc.). In many instances, where the ultimate parameter to be monitored is a physical distance (e.g., a tool dislodgement moving away from the reference location by a predetermined distance such as 1 mm), the threshold values defining an "abrupt" correlation change may be determined empirically (e.g., bench testing).

In addition, the dislodgement of the medical tool 26a may be the result of an external force applied to the medical tool. First, a portion of the medical tool 26a absorbs the external force and is deformed. Then, when the external force becomes large enough, the medical tool 26a is dislodged from its parked position. Therefore, the greater the number of MPS location sensors that are disposed and/or attached to the tool 26a, the better the information will be concerning a possible impending dislodgement. The earlier availability of the relevant information can be processed by the detection block 28 to provide an earlier detection of tool dislodgement (or impending tool dislodgement) based on the scenario described above. For example, a single MPS location sensor attached to the middle of the tool 26a might not move when the medical tool 26a is bent by an external force on an end thereof. In this situation, additional MPS sensors (e.g., sensor 24$_2$) can provide supplemental information, which is illustrated in the table of FIG. 5 as a series of P&O readings 60. Note, that even if there is no change in (x, y, z) (i.e., no dislodgement of the device away from the parked, reference location), the control unit is also configured to assess changes in the orientation. A change in orientation meeting predetermined criteria may be an indication of stress build-up in the device, which in turn may eventually translate into a movement in (x, y, z), or in other words, a dislodgement.

When using multiple MPS location sensors on a medical tool 26a, the remote MPS location sensors may or may not correlate to the movement of the parked end. The detection block 28 learns and records the patterns of motion indicated by the respective outputs from the MPS sensors (i.e., the tool motion), the ECG signal(s) (cardiac motion) and the PRS sensor (respiration motion and patient movements). When the tool 26a is equipped with multiple sensors and the output from one of them exhibits a different motion behavior, then the detection block 28 interprets that occurrence as a motion specific to that sensor. Through the foregoing, patterns can be learned using the outputs described above when the tool 26a is in the parked position. Thereafter, changes in the recorded patterns may be interpreted as dislodgement (or impending dislodgement).

In another aspect of the invention, a system and method is provided for detecting a prolapse condition in a guidewire from its desired position (i.e., position and orientation). As shown in FIG. 1, the main control 12 is configured though the prolapse detection block 30 to function as a prolapse condition detection apparatus. The disclosed system and method overcomes the disadvantages of the conventional approaches as described in the Background. Generally, an apparatus includes an MPS configured to constantly monitor the output of an MPS location sensor coupled to the tip of the guidewire. When the apparatus, based on the information from the MPS, determines that a prolapse alerting situation has occurred, according to the position and orientation vector of the guidewire tip, the apparatus generates an alarm signal (alarm block 32). The capability of detecting guidewire prolapse via the MPS location sensor reduces or eliminates the need for live (constant) fluoroscopy monitoring in order to detect the guidewire prolapse condition. Some examples of prolapse alerting situations include an abrupt change in the orientation of a motion vector of the guidewire tip or a guidewire tip motion vector that is a reverse duplication of an immediately prior guidewire tip motion vector. A further example of a prolapse alerting situation involves a condition where there is poor correlation between the motion vector of the distal end of the guidewire (i.e., as detected by an MPS location sensor) and the motion vector of the proximal end of the guidewire (i.e., as detected by a proximal motion detecting device) or in other words where the distal and proximal ends exhibit different motion patterns. A further example involves a device that includes multiple MPS location sensors. When the movement of one sensor exhibits abnormal behavior in view of the movement of another sensor, then the apparatus determines that a prolapse condition exists.

Figure 6A:
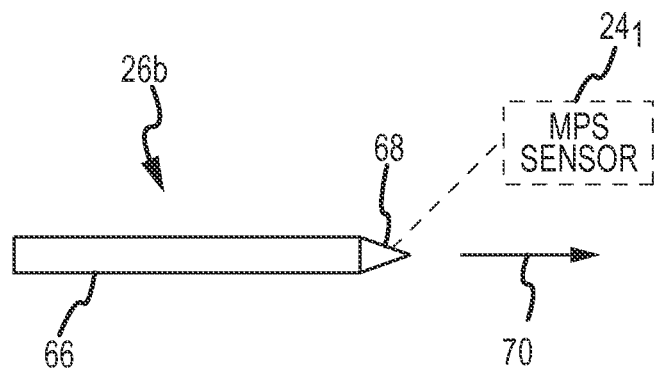
FIGS. 6A-6F are views of a distal portion of a guidewire shown in non-prolapse and prolapse conditions.
Figure 6B:
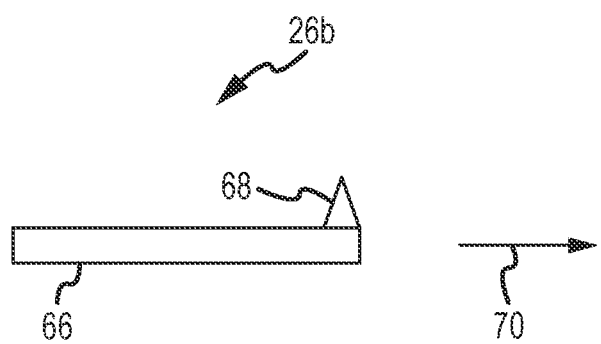
Figure 6C:
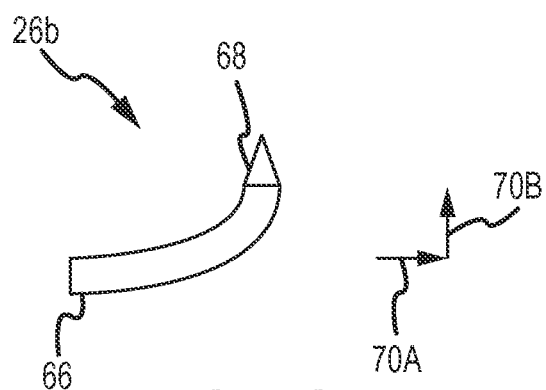
Figure 6D:
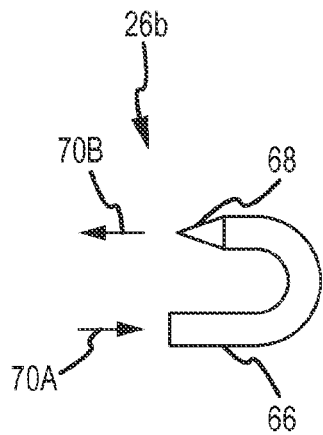
Figure 6E:
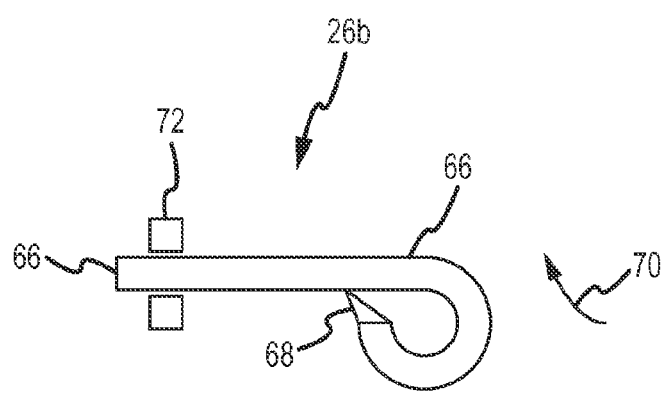
Figure 6F:
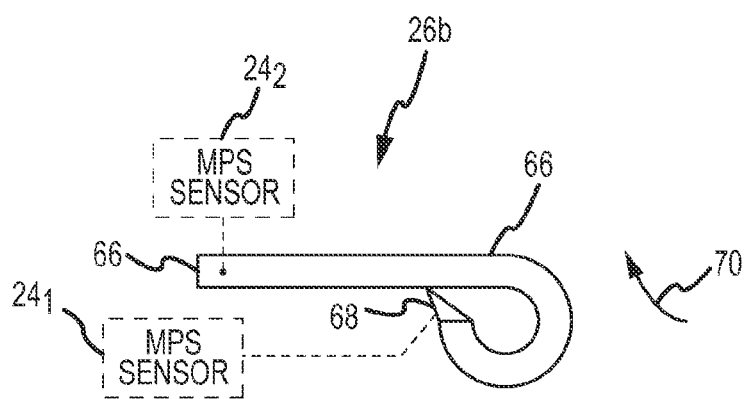
Figure 7:
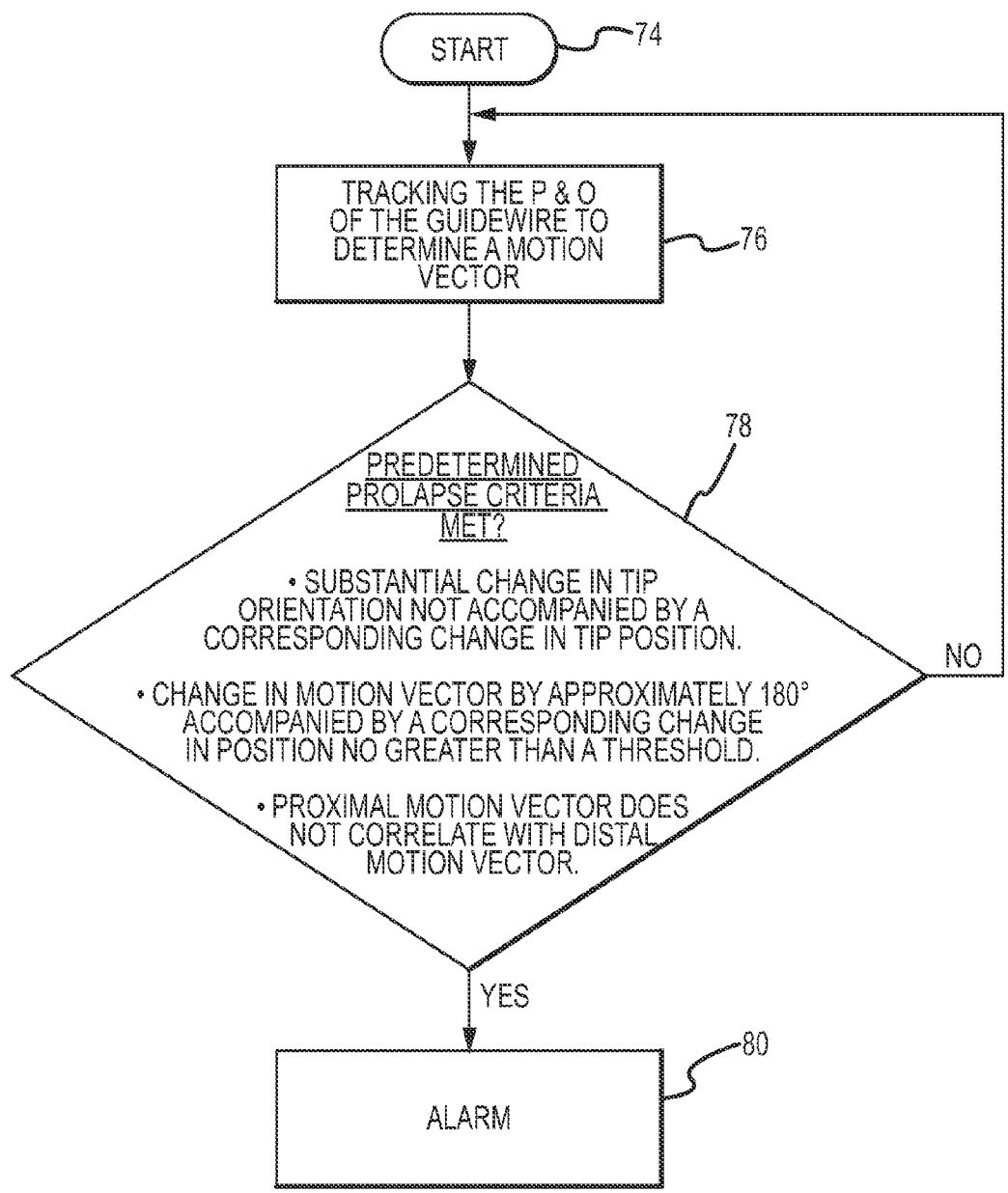
FIG. 7 is a flowchart showing a method for prolapse detection.

FIGS. 6A-6F are views showing the distal end of a guidewire in a non-prolapse condition and in a number of prolapse conditions and FIG. 7 is a flowchart of a method for detecting guidewire prolapse. FIG. 6A shows a subject medical device, guidewire 26b, in a non-prolapse condition. The guidewire 26b has a proximal end 66 and a distal end tip 68. An MPS location sensor 24$_1$ is coupled to the distal end or tip 68 and is configured for connection to the MPS 20 (e.g., via a connecting wire or the like). The MPS 20 is configured to sample (e.g., at periodic intervals) the output of the MPS sensor 24$_1$ to produce a series of position and orientation (P&O) readings indicative of the P&O of the distal tip 68. In addition, the series of P&O readings (or a portion thereof spanning a recent, predetermined time period, such as two seconds) collectively define a motion vector 70 of the guidewire tip 68. The determination of the motion vector may be performed by the MPS 20 or by the control 12.

FIG. 6B shows the guidewire 26b in a prolapse condition. The tip 68 is oriented in the upward direction, while the most recent motion vector 70 is directed to the right, indicating a change in the orientation of the tip 68. When the prolapse detection block 30 (best shown in FIG. 1) detects a significant enough change in the orientation of the tip 68, the control 12 generates an alarm signal, for example, to alert a physician who is controlling the guidewire 26b of the prolapse (or impending prolapse) condition.

The underlying principal of prolapse is spatial, and may occur during abrupt maneuvers as well as during smooth, gentle motion of the guidewire. Accordingly, the detection block 30 is configured to detect prolapse based on the spatial motion characteristics of the guidewire in preference to the temporal motion characteristics. More specifically, the detection block 30 is configured to determine the correspondence between the position and orientation at any particular time, as compared to a recent, previous time (i.e., the correspondence between the current and previous orientation and the motion direction). Two scenarios are common: (i) a significant change in the orientation of the distal tip 68 that is not accompanied by a corresponding change in position, which can happen if the tip 68 is caught by a bifurcation (i.e., vessel branching); and (ii) a turning of the tip 68 by about 180 degrees in orientation (plus or minus a predetermined degree range) with a relatively small change in position (e.g., on the order of magnitude of the diameter of the blood vessel in which the guidewire is being navigated). When the detection block 30 detects either of these scenarios indicative of prolapse, it signals the control 12 to generate the alarm signal.

In FIG. 6B, the orientation has changed about 90 degrees without any significant change in the tip position. Accordingly, per the criteria above, the detection block 30 will detect the prolapse condition and the control 12 will generate the alarm signal.

FIG. 6C also shows a prolapse (or impending prolapse) condition. In FIG. 6C, the current motion vector 70B is plotted next to the previous motion vector 70A. Again, the orientation of the guidewire tip 68 has changed by about 90 degrees while there is still a measurable yet relatively small change in the position of the tip 68. Accordingly, per the criteria set forth above, the detection block 30 will detect prolapse and the control 12 will then generate the alarm signal.

FIG. 6D is a further example of a prolapse condition of the guidewire tip 68 (e.g., the guidewire tip being turned-around in a blood vessel). The motion vector 70A represents the immediately previous motion vector while the motion vector 70B is the current motion vector. The direction of the motion vector 70B is substantially opposite that of the motion vector 70A or in other words the tip 68 has undergone about a 180 degree change in orientation. Moreover, the position of the distal tip 68 has not changed substantially, and assuming the reversed C-shaped guidewire 26b in FIG. 6D fits within the diameter of the blood-vessel being navigated, the detection block 30 confirms that the previously described criteria has been met and signals the control 12 to generate the alarm signal. In an embodiment, the control 12 is configured to determine whether the tip has undergone a change in orientation of about 180 degrees and whether the change in the position of the distal tip 68 is no greater than a predetermined threshold (i.e., the diameter of the lumen). The control 12 may be further configured to determine the predetermined threshold based on an image or electroanatomical model of the region of interest that contains the distal tip 68. Moreover, such an image may be obtained through fluoroscopy.

FIG. 6E shows another example of the guidewire 26b in a prolapse condition. A proximal motion detecting device 72 is disposed, for example, at a proximal hub portion of the system 10. The device 72 is configured to detect the proximal motion of the guidewire 26b and produce a signal indicative of the guidewire proximal motion, which is provided to the prolapse detection block 30. In an embodiment, the device 72 may comprise a sub-system configured to optically detect the motion of the guidewire and provide a motion indicative signal to the prolapse detection block 30. In a further embodiment, the device 72 may be disposable.

The proximal motion detecting device 72 may be configured to detect the length of guidewire 26b passing past the proximal motion device 72 and generate a length-indicative signal that is provided to the detection block 30. In addition, as already described above, the MPS 20 also monitors the position of the distal tip 68 (using MPS $24_1$) from which the motion of (and thus the length traversed by) the distal end 68 may be determined by the detection block 30. The block 30 detects when a predetermined amount of advancement of the guidewire 26b at the proximal end is accompanied by no more than a predetermined maximum advancement at the distal end. When the block 30 determines that this criteria has been met, it signals the control 12 to generate the alarm.

In FIG. 6E, the motion vector 70 of the tip 68 is typical of the situation when the tip 68 has encountered an obstacle (not shown) and has turned backwards, such that the distal tip motion vector 70 indicates very little advancement while at the same time the output of the proximal motion detecting device 72 indicates that the guidewire proximal end has made greater advancement. The detection block 30 is configured to assess the distal tip P&O readings and generate a distal end motion vector. The proximal end motion readings (from device 72) are used by detection block 30 to generate a proximal end motion vector. The detection block 30 is configured to compare the distal and proximal end motion vectors and determine when the level of correlation is poor, which is indicative of prolapse. The detection block 30 signals the main control 12 to then generates the alarm.

FIG. 6F shows another example of the guidewire 26b (in a prolapse condition) that includes multiple MPS location sensors. A further MPS location sensor $24_2$ is coupled to the proximal end of the guidewire 26b, in which case the MPS 20 is configured to provide P&O readings that track the proximal end of the guidewire. The series of acquired proximal-end P&O readings directly define the motion of the proximal end. In addition, the guidewire 26b also includes the first MPS location sensor $24_1$ at the distal end (FIG. 6A also) and the MPS 20 provides a series of distal-end P&O readings that directly define the motion of the distal end.

In FIG. 6F, the motion vector 70 of the tip 68 is typical of the situation when the tip 68 has encountered an obstacle (not shown) and has turned backwards, such that the distal tip motion vector 70 indicates very little advancement while at the same time the output of the proximal-end MPS location sensor $24_2$ indicates that the guidewire proximal end has made greater advancement. The detection block 30 is configured to assess the distal tip P&O readings and generate a distal end motion vector. The P&O readings corresponding to the proximal end MPS sensor $24_2$ are used by detection block 30 to generate a proximal end motion vector. The detection block 30 is configured to compare the distal and proximal end motion vectors and determine when the level of correlation is poor, which is indicative of prolapse. The detection block 30 signals the main control 12 to then generate the alarm. The detection block 30 may be configured to detect a plurality of examples of abnormal behavior indicative of prolapse, including but not limited to (1) when one of the MPS sensors $24_1$, $24_2$ advances and the other does not; (2) when one of the MPS location sensors $24_1$, $24_2$ doubles-back on the other; (3) when the second sensor (e.g., proximal-end sensor) does not follow the path of the first sensor (e.g., the distal-end sensor); and (4) when the distance between the sensors $24_1$, $24_2$ changes or when the distance between the sensors falls below a predetermined value.

FIG. 7 is a flow chart of a method for detecting prolapse, which begins in step 74. In step 74, the prolapse detecting feature of detection block 30 may be activated in the control 12 via either a user input or alternatively may be activated automatically. The method then proceeds to step 76.

In step 76, the position of the distal tip 68 of the guidewire 26*b* is tracked by the MPS 20 wherein the detection block 30 may record a series of P&O readings obtained over time. In an embodiment, the detection block 30 is configured to determine a motion vector of the guidewire distal tip using P&O readings acquired during a most recent time interval (e.g., two seconds). It should be understood that this step may be alternatively performed by the MPS 20. The method then proceeds to step 78.

In step 78, the detection block 30 of the control 12 assesses the motion of the guidewire 26*b* (including the most recent motion vector) against predetermined detection criteria to determine whether a prolapse condition exists. The predetermined criteria may include: (i) whether there has been a substantial change in the tip orientation not accompanied by a corresponding change in the tip position; (ii) whether there has been a change in the motion vector by approximately 180 degrees (plus or minus a predetermined guard band) accompanied by a corresponding change in position of not more than a predetermined threshold amount (e.g., the diameter of a blood vessel); and (iii) whether the proximal motion vector of the guidewire fails to adequately correlate with the distal motion vector of the guidewire. If the predetermined criteria for any of these situations is met ("YES"), then the method branches to step 80, in which case a suitable alert or alarm is generated.

Alternatively, if the criteria for none of the individual situations described above is met ("NO"), then the method branches to step 76, where the detection block 30 continues to track the P&O of the distal tip of the guidewire 26*b* to recalculate the distal tip motion vector again for a new period of time. The method iterates through the steps, each time checking prevailing guidewire motion vectors and/or behavior against the predetermined prolapse detection criteria described above.

Through the foregoing tool dislodgement and prolapse condition detection features, medical procedures can be performed using are reduced amount of live fluoroscopy by virtue of eliminating the need for fluoroscopy for the purpose of implementing these detection features.

Figure 8:
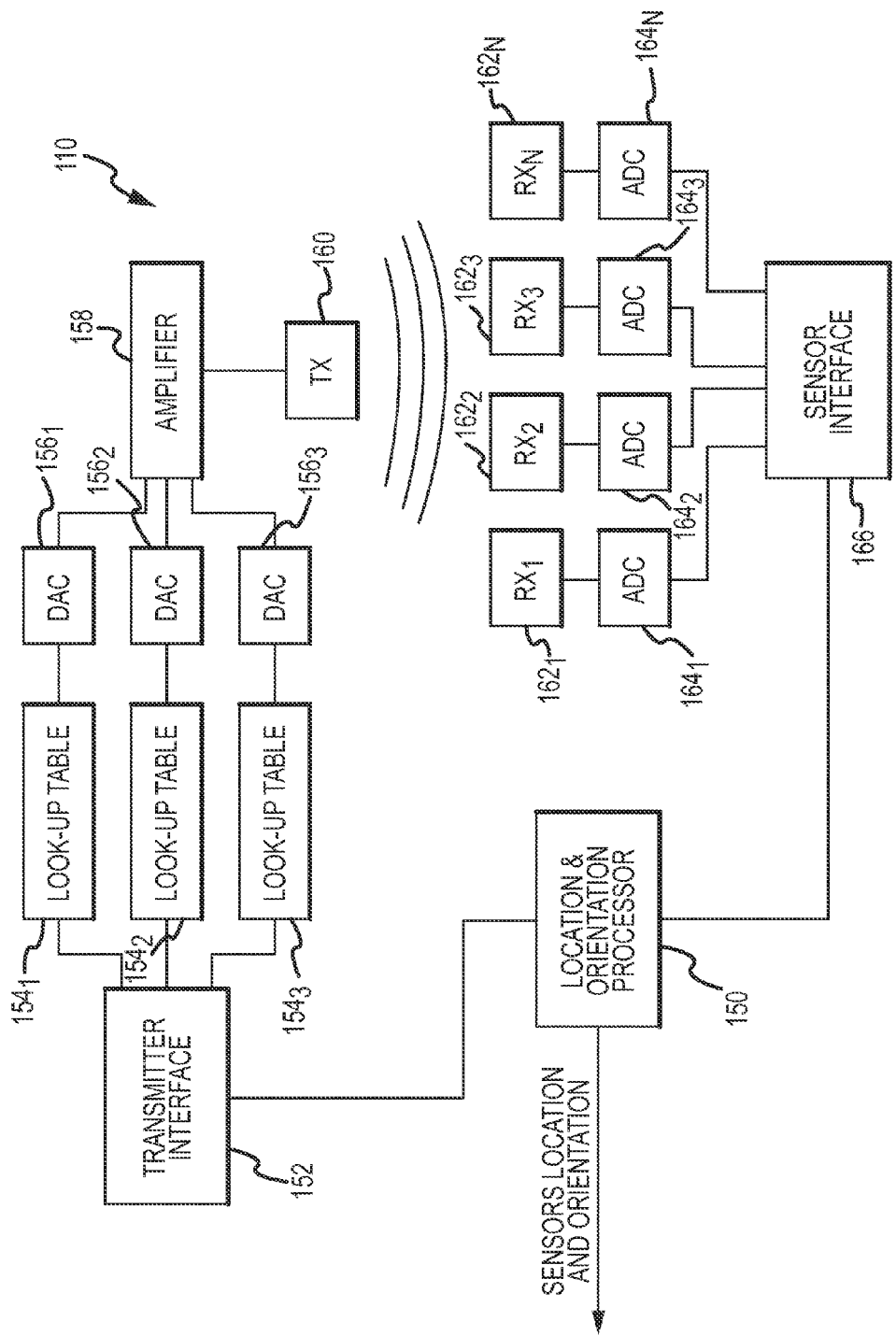
FIG. 8 is a schematic and block diagram view of one exemplary embodiment of a medical positioning system (MPS) used for the localization system.

FIG. 8 is a schematic and block diagram of one exemplary embodiment of MPS system 20, designated as an MPS system 108, as also seen by reference to U.S. Pat. No. 7,386,339, referred to above, and portions of which are reproduced below, which generally describes, at least in part, the gMPS™ medical positioning system commercially offered by MediGuide Ltd. It should be understood that variations are possible, for example, as also seen by reference to U.S. Pat. No. 6,233,476 entitled MEDICAL POSITIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, this description is exemplary only and not limiting in nature.

MPS 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that the system 10, particularly control 12, as described above may include conventional processing apparatus known in the art, capable of executing pre-programmed instructions stored in an associated memory, all performing in accordance with the functionality described herein. It is contemplated that the methods described herein, including without limitation the method steps of the described embodiments, may be programmed, with the resulting software being stored in an associated memory and where so described, may also constitute the means for performing such methods. Implementation in software in view of the foregoing enabling description would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for detecting dislodgement of a medical tool from a reference location within a patient's body, comprising:
   a localization system configured to output a location reading indicative of a location of the medical tool in a coordinate system based on a signal from a location sensor included in the medical tool, wherein said location reading comprises at least one of a position and orientation (P&O); and
   a control configured to determine a motion of the medical tool as a function of a plurality of said location readings, said control being further configured to determine when said determined medical tool motion satisfies predetermined tool motion conditions indicative of dislodgement based on at least one of said plurality of location readings of said medical tool and generating an alarm signal, wherein said predetermined motion conditions comprise at least a predetermined threshold distance beyond which the medical tool must move away from the reference location wherein the reference location within the patient's body has a reference coordinate in said coordinate system, and wherein the reference location comprises an initial one of said medical tool location readings according to an initialization event, and wherein said control compares a medical tool coordinate and said reference coordinate with respect to said predetermined threshold distance to determine when said predetermined motion conditions are satisfied, said predetermined motion conditions are determined according to at least one factor selected from the group comprising a type of medical procedure, a type of medical tool, a parking position of the medical tool, and a preference of a physician.

2. The apparatus of claim 1 wherein said medical tool includes a first location sensor and a second location sensor, said localization system being configured to produce a first plurality of location readings in accordance with said first location sensor output and a second plurality of location readings in accordance with said second location sensor output.

3. The apparatus of claim 2 wherein said control is configured to determine the presence of an external force on the medical tool by detecting a displacement between the tool and the reference location using the motions indicated by the first and second plurality of location readings.

4. The apparatus of claim 2 wherein said control is configured to determine said tool motion further as a function of said first plurality and said second plurality of location readings.

5. The apparatus of claim 1 wherein said location sensor comprises a magnetic field sensor configured to detect one or more characteristics of a magnetic field in which said location sensor is disposed, said signal from said location sensor being indicative of said detected one or more characteristics.

6. The apparatus of claim 5 wherein said magnetic field comprises an alternating current (AC) magnetic field.

7. The apparatus of claim 1 wherein said reference location is an anatomical location within said patient's body.

8. An apparatus for detecting dislodgement of a medical tool from a reference location corresponding to an anatomical location within a patient's body, comprising:
   a localization system configured to output a tool location reading indicative of a location of the medical tool in a coordinate system wherein said tool location reading comprises at least one of a position and orientation (P&O);
   at least one of (i) a patient reference sensor for affixation to the patient and configured to be coupled to said localization system to produce said plurality of patient reference sensor location readings indicative of patient respiration-induced and patient body movement-induced components of the reference location motion and (ii) an electrocardiogram monitor configured to produce said electrocardiogram signals indicative of a heartbeat-induced movement component of the reference location motion;
   a control configured to determine a motion of the medical tool as a function of a plurality of said tool location readings, said control being configured to determine a first correlation between the tool motion and the motion of the reference location during a learning stage when the medical tool is parked at the reference location, wherein the reference location within the patient's body has a reference coordinate in said coordinate system, and wherein the reference location comprises an initial one of said medical tool location readings according to an initialization event, wherein said control is configured to determine said first correlation by calculating the first correlation between the tool location readings and said at least one of (i) said plurality of patient reference sensor location readings and (ii) said electrocardiogram signals wherein said control is further configured to determine said first correlation by comparing said plurality of said tool location readings and said at least one of said patient reference sensor location readings and said electrocardiogram signals relative to a common time-line, said control being further configured to determine, after the learning stage, a second correlation between the tool motion and reference location motion, said control being further configured to generate an alarm signal indicative of dislodgement when a comparison of the first correlation and the second correlation meets predetermined dislodgement detection criteria.

9. The apparatus of claim 8 wherein said medical tool includes a first location sensor configured for coupling to said localization system for producing a first plurality of location readings and a second location sensor configured for coupling to said localization system for producing a second plurality of location readings, said control being is further configured to determine a presence of an external force on the medical tool by detecting a displacement between said medical tool and said reference location using the motions indicated by the first and second plurality of location readings.

10. The apparatus of claim 9 wherein said control is configured to assess changes in an orientation of one of said first and second location sensors, wherein said control is configured to detect impending dislodgement when changes in said orientation meet predetermined criteria.

11. The apparatus of claim 8 wherein said patient reference sensor location reading comprises at least one of a position and orientation (P&O).

12. The apparatus of claim 11 wherein said predetermined criteria includes a change between the first correlation and the second correlation exceeding a predetermined threshold in under a predetermined time period.

13. The apparatus of claim 12 wherein said predetermined threshold and said predetermined time period are determined according to at least one factor selected from the group comprising a medical procedure type, a medical tool type, the parking position of the medical tool, a characteristic of the patient and a preference of a physician and wherein said characteristic of the patient is at least one selected from the group comprising age, weight and gender.

14. The apparatus of claim 11 wherein said medical tool includes a first location sensor configured for coupling to said localization system for producing a first plurality of location readings and a second location sensor configured for coupling to said localization system for producing a second plurality of location readings, said tool motion comprises the respective movements of said first and second location sensors,
said first correlation comprises a pair of first correlations associated with the movements of said first and second location sensors respectively and taken with respect to at least one of said patient reference sensor location readings and said electrocardiogram signals during said learning stage,
said second correlation comprises a pair of second correlations associated with the movements of said first and second location sensors respectively and taken with respect to at least one of said patient reference sensor location readings and said electrocardiogram signals during a monitoring stage,
said control being further configured to determine, for each of said first and second location sensors, a respective change between first and second correlations associated with each of said first and second location sensors and to generate said alarm signal when at least one of said determined correlation changes meet said predetermined dislodgement detection criteria.

15. The apparatus of claim 8 wherein said control is configured to begin said learning stage in response to said initialization event.

16. The apparatus of claim 15 wherein said initialization event comprises an input start signal and wherein said control includes an input/output interface configured to receive said input start signal from a user.

17. The apparatus of claim 15 wherein said control determines said initialization event automatically when said medical tool has been in a same position for a time period exceeding a predetermined value.

18. The apparatus of claim 8 wherein said control, using said predetermined dislodgement detection criteria, is configured to distinguish between a first situation where respective movements of said medical tool and the reference location indicate dislodgement and a second situation where said medical tool and said reference location are moving together but with no relative movement therebetween.

19. The apparatus of claim 8 wherein said alarm signal comprises at least one of a visual indication, a verbal audible indication, a non-verbal audible indication, a tactile indication, and a combination of one or more of the foregoing indications.

20. The apparatus of claim 8, wherein said control is further configured to determine when said tool motion satisfies predetermined tool motion conditions indicative of dislodgement and generating said alarm signal, wherein said predetermined motion conditions are determined according to at least one factor selected from the group comprising the type of medical procedure, the type of medical tool, the parking position of the medical tool, a characteristic of the patient and a preference of a physician and wherein said characteristic of the patient is at least one selected from the group comprising age, weight and gender.

21. The apparatus of claim 20 wherein said medical tool includes a first location sensor and a second location sensor, said localization system being configured to produce a first plurality of location readings in accordance with said first location sensor output and a second plurality of location readings in accordance with said second location sensor output.

22. The apparatus of claim 21 wherein said control is further configured to determine a presence of an external force on the medical tool by detecting a displacement between the tool and the reference location using the motions indicated by the first and second plurality of location readings.

23. The apparatus of claim 21 wherein said control is further configured to determine said medical tool motion further as a function of said first plurality and said second plurality of location readings.

24. The apparatus of claim 8 wherein said medical tool includes a magnetic field location sensor configured to detect one or more characteristics of a magnetic field in which said location sensor is disposed and output a signal indicative of said detected one or more characteristics, wherein said localization system is configured to output said tool location reading based on at least said signal.

25. The apparatus of claim 24 wherein said magnetic field comprises an alternating current (AC) magnetic field.

* * * * *